United States Patent
Zhong et al.

(10) Patent No.: US 6,297,005 B1
(45) Date of Patent: Oct. 2, 2001

(54) DE NOVO PRIMING ACTIVITY OF HEPATITIS C VIRUS REPLICASE

(75) Inventors: Weidong Zhong, Royersford, PA (US); Zhi Hong, Nanuet, NY (US); Annette Schettino Uss, Lebanon Township; Johnson Y. N. Lau, Warren, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/305,185

(22) Filed: May 4, 1999

(51) Int. Cl.$^7$ .................................................. C12Q 1/68
(52) U.S. Cl. ........................ 435/5; 536/233; 536/24.32
(58) Field of Search ............................... 435/5; 536/23.3, 536/24.32, 23.72

(56) References Cited

FOREIGN PATENT DOCUMENTS

WO 96/37619    11/1996    (WO) .

OTHER PUBLICATIONS

Arnold and Cameron, J. Biol. Chem. 274:2706–2716 (1999).
Ferrari et al., J. Virol. 73: 1649–54 (1999).
Kao et al., Virology 253: 1–7 (1999).
Al et al., Virus Res. 53: 141–149 (1998).
Lohmann et al., Virology 249: 108–118 (1998).
Paul et al., Nature 393:280–284 (1998).
Reichard et al., Lancet 351: 83–87 (1998).
Wyatt et al., J. Virol. 72: 1725–1730 (1998).
Yan et al., Protein Sci. 7: 837–847 (1998).
Zhong et al., J. Virol. 72:9365–9369 (1998).
Joyce and Steitz, Annu. Rev. Biochem. 63: 777–822 (1997).
Lohmann et al., J. Virol 71: 8416–8428 (1997).
Marcellin et al., Ann. Intern. Med. 127: 875–881 (1997).
Yao et al., Nat. Struct. Biol. 4: 463–467 (1997).
Yuan et al., Biochem. Biophys. Res. Commun. 232: 231–235 (1997).
Behrens et al., EMBO J. 15: 12–22 (1996).
De Francesco et al., Methods Enzymol. 275: 58–67 (1996).
Kao et al., J. Med. Virol. 50: 303–308 (1996).
Kim et al., Cell 87: 343–355 (1996).
Love et al., Cell 87: 331–342 (1996).
Tanji et al., J. Virol. 69: 1575–1581 (1995).
Alter and Mast, Gastroenterol. Clin. North Am. 23: 437–455 (1994).
Iwarson, S., FEMS Microbiol. Rev. 14: 201–204 (1994).
Kew, M., FEMS Microbiol. Rev. 14: 211–220 (1994).
Purcell, FEMS Microbiol. Rev. 14: 181–192 (1994).
Shimizu et al., J. Virol. 68: 1494–1500 (1994).
van der Poel, C.L., Curr. Stud. in Hematol. Blood Transf., H.W. Reesink, ed., (Basel: Karger), No. 61, pp. 137–163 (1994).
Bartenschlager et al., J. Virol. 67: 3835–3844 (1993).
Grakoui et al., J. Virol. 67: 2832–2843 (1993).
Grakoui et al., J. Virol. 67: 1385–1395 (1993).
Tomei et al., J. Virol. 67: 4017–4026 (1993).
Farci et al., Science 258: 135–140 (1992).
Choo et al., Proc. Natl. Acad. Sci. USA 88: 2451–2455 (1991).
Takamizawa et al., J. Virol., 65: 1105–1113 (1991).
Kato et al., Proc. Natl. Acad. Sci. USA 87: 9524–9528 (1990).
Saito et al., Proc. Natl. Acad. Sci. USA 87: 6547–6549 (1990).
Choo et al., Science 244: 359–362 (1989).
Kuo et al., Science 244: 362–364 (1989).

*Primary Examiner*—Scott W. Houtteman
(74) *Attorney, Agent, or Firm*—David B. Schram

(57) ABSTRACT

The present invention relates to identification of a novel, de novo priming activity of hepatitis C virus replicase. This activity can be used to screen for anti-HCV replicase compounds, or to characterize the biological relevance of lead compounds that have already been identified.

20 Claims, 3 Drawing Sheets

DE NOVO PRIMING ACTIVITY OF HEPATITIS C VIRUS REPLICASE

FIELD OF THE INVENTION

The present invention relates to identification of a novel, de novo priming activity of hepatitis C virus replicase. This activity can be used to screen for anti-HCV replicase compounds, or to characterize the biological relevance of lead compounds that have already been identified.

BACKGROUND OF THE INVENTION

Infection by hepatitis C virus (HCV) is a compelling human medical problem. HCV is recognized as the causative agent for most cases of non-A and non-B hepatitis, with an estimated prevalence of 170 million cases (i.e., 2–3%) globally [Choo, et al., Science, 244: 359–362 (1989); Kuo, et al., Science, 244: 362–364 (1989); Purcell, FEMS Microbiology Reviews, 14: 181–192 (1994); Van der Poel, C. L., Current Studies in Hematology and Blood Transfusion, H. W. Reesink, Ed., (Basel: Karger), pp. 137–163 (1994)]. Four million individuals may be infected in the United States alone [Alter, and Mast, Gastroenterol. Clin. North Am., 23: 437–455 (1994)].

Upon first exposure to HCV only about 10% or less of infected individuals develop acute clinical hepatitis, while others appear to resolve the infection spontaneously. In the most instances, however, the virus establishes a chronic infection that persists for decades [Iwarson, FEMS Microbiology Reviews, 14: 201–204 (1994)]. This usually results in recurrent and progressively worsening liver inflammation, which often leads to more severe disease states such as cirrhosis and hepatocellular carcinoma [Kew, FEM Microbiology Reviews, 14: 211–220 (1994); Saito, et al., Proc. Natl. Acad. Sci. USA 87:6547–6549 (1990)]. Currently, there are no broadly effective treatments for the debilitating progression of chronic HCV.

The HCV genome encodes a polyprotein of 3010–3033 amino acids [Choo, et al. Proc. Natl. Acad. Sci. USA, 88: 2451–2455 (1991); Kato, et al., Proc. Natl. Acad. Sci. USA, 87: 9524–9528 (1990); Takamizawa, et al., J. Virol., 65: 1105–113 (1991)]. The HCV nonstructural (NS) proteins provide catalytic machinery for viral replication. The NS proteins are derived by proteolytic cleavage of the polyprotein [Bartenschlager, et al., J. Virol., 67: 3835–3844 (1993); Grakoui, et al. J. Virol, 67: 2832–2843 (1993); Grakoui, et al., J. Virol., 67: 1385–1395 (1993); Tomei, et al., J. Virol., 67: 4017–4026 (1993)].

Current therapies with alpha interferon alone and the combination of alpha interferon-ribavirin have been shown to be effective in a portion of patients with chronic HCV infection [Marcellin et al., Ann. Intern. Med. 127:875–881 (1997); Reichard et al., Lancet 351:83–87 (1998)]. Vaccine development has been hampered by the high degree of immune evasion and the lack of protection against reinfection, even with the same inoculum [Farci et al., Science 258: 135–140 (1992); Kao et al., J. Med. Virol. 50:303–308 (1996); Shimizu et al., J. Virol. 68:1494–1500 (1994); Wyatt et al., J. Virol. 72:1725–1730 (1998)]. Development of small molecule inhibitors directed against specific viral targets has thus become the focus of anti-HCV research. The determination of crystal structures for NS3 protease [Kim et al., Cell 87:343–355 (1996); Love et al., Cell 87:331–342 (1996); Yan et al., Protein Sci. 7:837–847 (1998)] and NS3 RNA helicase [Yao et al., Nat. Struct. Biol. 4:463–467 (1997)] has provided important structural insights for national design of specific inhibitors.

One key enzyme encoded by HCV is NS5B, which has been shown to be an RNA-dependent RNA polymerase (RdRp) [Al et al., Virus Res. 53: 141–149 (1998); Behreus et al., EMBO J. 15:12–22 (1996); DeFrancesco et al., Methods Enzymol. 275:58–67 (1996); Lohmann et al., J. Virol 71:8416–8428 (1997); Yuan et al., 1997, Biochem. Biophys. Res. Commun. 232:231–235 (1997); Ferrari et al., J. Virol. 73:1649–54 (1999)] NS5B is thus believed to be responsible for HCV genome replication. Cellular localization studies revealed that NS5B is membrane associated and distributed in the perinuclear region [Hwang et al., Annu. Rev. Biochem. 63:777–822 (1997)]. This coincides with the distribution of NS5A [Tanji et al., J. Virol. 69:1575–1581 (1995)], suggesting that NS5A and NS5B may stay together after proteolytic cleavage at the NS5A/NS5B junction. It has been postulated that the nonstructural proteins of HCV (NS3 to NS5B) may assemble into membrane-associated replication complexes that are competent for authentic RNA genome replication.

By itself, HCV NS5B RdRp appears to lack specificity for HCV RNA and can "copy back" heterologous nonviral RNA. This lack of specificity for HCV RNA may reflect the notion that additional viral or cellular factors are required for specific recognition of the replication signal, most likely present at the 3' untranslated region. Recent studies by Lohmann et al. (supra) demonstrated that NS5B alone can replicate the entire HCV genome via a copy-back mechanism initiated from the end of the 3' untranslated region.

The ability of recombinant NS5B from bovine viral diarrhea virus (BVDV) to initiate RNA synthesis by a primer-independent mechanism has recently been reported [Kao et al., Virology, 23, pp. 1–7 (1999)]. De novo initiation of RNA synthesis is likely to be the mode of initiation of BVDV replication in an infected cell. Kao et al. (supra) demonstrates that BVDV RdRp can preferentially initiate RNA synthesis by a de novo mechanism from short templates containing the signals for the initiation of genomic positive strand synthesis, and characterizes the requirements for the interaction between RdRp and the initiation site.

To date, there has been no report of de novo initiation of RNA synthesis by HCV NS5B.

Thus, there is a need in the art to resolve the current uncertainty concerning HCV genome replication.

There is a further need in the art to develop effective therapeutic strategies to inhibit viral specific features of HCV replicase.

The present invention addresses these and other needs in the art.

SUMMARY OF THE INVENTION

The present invention advantageously establishes that hepatitis C virus (HCV) replicase activity can proceed in a primer-independent mode, e.g, by de novo priming. This priming activity, which depends on the template sequence and, critically, on the concentration of the initial one to two complementary nucleotide triphosphates, can be harnessed for various primary, and especially secondary, screening assays for anti-HCV compounds. In particular, the present invention permits one to determine whether an HCV NS5B binding compound or inhibitor is capable of selectively blocking de novo priming and primer independent replicase activity, without adversely affecting host cell replication and transcription processes.

Thus, in one aspect, the invention provides an assay system for primer-independent HCV replicase (NS5B) activity, which comprises an RNA template that is incapable of self-priming, an enzymatically active HCV non-structural protein 5B (NS5B), ATP, GTP, CTP, and UTP nucleotide triphosphates (NTPs), wherein one of the NTPs is radiolabeled.

The invention further provides a method for detecting primer-independent HCV replicase activity, which method comprises detecting the presence of a nucleic acid synthesized by an HCV non-structural protein 5B (NS5B) on an RNA template that is incapable of self-priming (copy-back) RNA synthesis in the presence of ATP, GTP, CTP, and UTP nucleotide triphosphates (NTPs), wherein one of the NTPs is radiolabeled.

The invention further provides an optimal assay buffer for detecting the primer-independent HCV replicase activity.

The assay system and method permit testing candidate compounds for the ability to inhibit de novo initiation by HCV NS5B. Thus, in specific embodiments, a test compound is present in the assay system or method.

Thus, one object of the invention is to provide an assay system for primer-independent HCV replicase activity.

Another object of the invention is to provide a method for determining whether an HCV replicase can function in a primer-independent manner, as well as an optimal reaction buffer for detecting the activity.

These and other objects of the invention have been achieved, as described in further detail in the accompanying drawings and the following Detailed Description of the Invention.

DETAILED DESCRIPTION OF THE INVENTION

Figure 1:
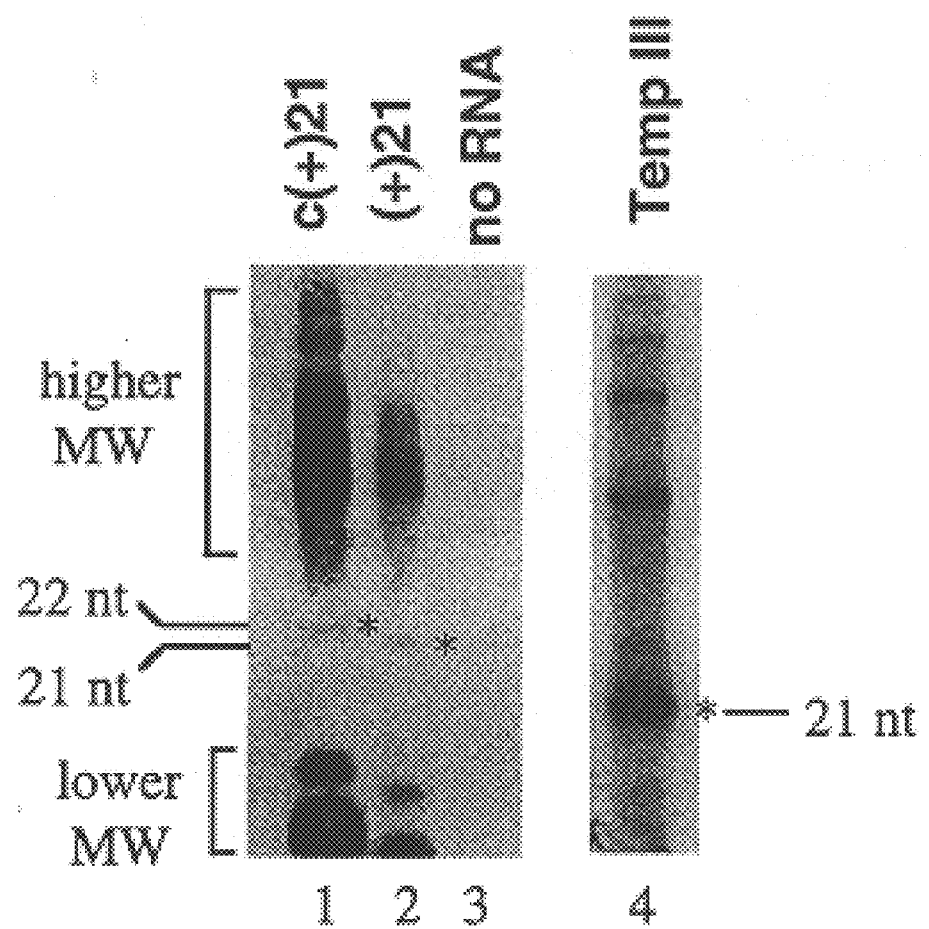
FIG. 1 shows the results of an in vitro priming/initiation assay in the presence of the c(+)21 (lane 1), (+)21 (lane 2) and Temp III (lane 4) RNA templates (SEQ ID NOS: 2, 1 and 3, respectively) or in the absence of any template (lane 3). * indicates a template sized product. All the RNA templates contain dideoxy nucleotides at the 3' terminus to prevent copy-back RNA synthesis.

The invention is based, in part, on the discovery that a recombinant HCV NS5B protein is able to initiate RNA replication via a de novo priming mechanism in a primer-independent fashion. To demonstrate this de novo priming activity, three RNA templates were chemically synthesized with a dideoxy-nucleotides (2', 3') at the 3' end in order to eliminate any self-priming via a "copy-back" mechanism.

HCV NS5B RdRp was able to utilize these modified RNA templates to initiate RNA replication, producing RNA products of different sizes. Monomer-size products represent the full-length RNA copies of the input templates, which can only result from primer-independent de novo initiation. Such an initiation of RNA replication directly from nucleotides, represents a novel priming activity. This de novo RNA replication by HCV NS5B required high concentrations of nucleoside triphosphates corresponding to +1 and +2 positions from the 3' ends. This suggests that de novo priming at the 3' end of the RNA templates is concentration sensitive and the priming step may be a rate-limiting one during RNA replication.

Identification of this intrinsic enzymatic property of HCV NS5B establishes the basis for assays to test antiviral compounds specifically targeting priming and initiation of replication. This may provide a unique window of opportunity to develop more potent and biologically relevant inhibitors of HCV.

General Definitions

As used herein, the term "de novo" refers to a primer independent mechanism for initiating RNA synthesis in a template-dependent fashion.

The term "assay system" as used herein refers to an experimental arrangement designed to measure NS5B activity. It can be in a high throughput mode, or an individual assay mode, depending on whether it is adapted for screening or for elucidating mechanisms of activity, for example.

An "RNA template" is an oligonucleotide, preferably of ribonucleotides (HCV NS5B does not use a DNA template efficiently), having a sequence that permits replication by NS5B. Preferably an RNA template of the invention is modified to prevent any copy-back priming (i.e., self-priming from the 3' end of the oligonucleotide). In a specific embodiment, the RNA template has a sequence similar to the 3' end of the HCV genome.

NS5B as used herein refers to the gene product of the last open reading frame of the hepatitis C virus genome. It generally corresponds to amino acid residues 2420–3010 of the HCV polyprotein [see, e.g., Behrens et al., EMBO J. 15:12–22 (1997)]. The protein has a molecular weight of 65 kD, and demonstrates both template dependent (RdRp; RNA dependent RNA polymerase) and template independent (TNTase) catalytic addition of ribonucleotides to the 3' termini of exogenous RNA in a $Mg^{2+}$-dependent process [see International Patent Publication WO 96/37619; Lohmann et al., Virology 249:108–118 (1998)]. $Mn^{2+}$ can be substituted for $Mg^{2+}$, and indeed appears to be preferred [Ferrari et al., J. Virol. 73:1649–54 (1999)]. Thus, an assay buffer that supports replication activity (i.e., RNA polymerization or the catalytic addition of ribonucleotides to the 3' termini of exogenous RNA) requires a divalent cation such as $Mg^{2+}$ or, preferably, $Mn^{2+}$. Gliotoxin inhibits HCV NS5B RdRp in a dose dependent manner [Ferrari et al., supra]. The ability of NS5B to polymerize ribonucleotides may be referred to as polymerase or as replicase activity.

A nucleotide triphosphate refers to ribonucleotide substrates of the NS5B. A radiolabel on a ribonucleotide triphosphate can be $^{33}$P or $^{32}$P, with the latter providing a stronger signal. Other radioisotopes can also be used, including but not limited to tritium ($^{3}$H) and carbon 12 ($^{12}$C). Other types of labels are likely to interfere unacceptably with enzymatic activity, and are therefore not desirable. Labeling of the $\alpha$-P will result in incorporation of the label with each added NTP. Labeling of the $\gamma$-P will result in labeling of only the initial NTP, since the γ-P is lost with pyrophosphate during polymerization by the replicase.

In a specific embodiment, the term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term about or approximately depends on the particular system under study, and can be readily appreciated by one of ordinary skill in the art.

Various aspects of the invention are disclosed in greater detail in the following sections related to NS5B, preparation of oligonucleotide templates, and assays. The headings (bold), subheadings (bold, italics), and sections of the application are provided to facilitate understanding of the invention, and are not intended to be limiting.

HCV Replicase (NS5B)

HCV NS5B for use in the assays of the present invention can be obtained from any source, although recombinant production is preferred to ensure an adequate supply of the enzyme for study.

In a preferred embodiment, NS5B is expressed in *E. coli* as a soluble product lacking the hydrophobic C terminus, and particularly the tetraleucine motif responsible for the solubility profile of full-length NS5B [Ferrari et al., J. Virol. 73:1649–54 (1999)].

In this specific embodiment, a consensus NS5B of HCV-1b was cloned from the BK isolate. A computer intensive approach was undertaken to identify the non-consensus mutations in NS5B of the BK isolate. The amino acid sequence of NS5B (BK) was compared to 16 NS5B proteins from different genotypes and subtypes. Four isolates representing genotype 1 subtype a (HCV-1a) and five from HCV-1b were used. The rest were from HCV-2a, 2b, 3a, 3b, 4a, 5a and 6a. Two potential non-consensus mutations were identified: one T at position 329, the other V at position 338 (numbered according to the sequence of unmodified NS5B). The corresponding amino acids in all other isolates were V and A respectively, which are consensus among different genotypes. These mutations were likely introduced into the cDNA clones isolated during reverse transcriptase and polymerase chain reaction (RT-PCR). RT-PCR is a commonly used method to isolate HCV cDNA clones, but this methods lacks a proof-reading process, which is required to prevent mis-incorporations (or errors) in the cDNA clones. Such mis-incorporations often result in mis-sense mutations at the amino acid level which lead to functional defects in the protein products of HCV.

To repair these non-consensus mutations, site-directed mutagenesis using the "Quick Change" mutagenesis kit (Stratagene, CA) was performed. The resulting clone was verified for correctness by direct sequencing and thus represented the consensus clone of NS5B of the BK isolate. This approach of generating consensus clones has been proven to be essential to obtain biologically validated and functionally correct clones of HCV. This consensus NS5B was subcloned into pET-21b (Novagen) between NheI and BamHI sites. Two codons were engineered at the N-terminus, coding for "MA", replacing the native amino acids (SM) at the N-terminus of NS5B. The C-terminal 21 amino acids were removed to improve the solubility [Ferrari et al., J. Virol. 73:1649–54 (1999)]. A polyhistidine tag (GSHHHHHH) (SEQ ID NO:4) was engineered to replace the C-terminal domain which facilitates the purification of the enzyme.

Alternatively, a PCR product containing the cDNA region encoding amino acids 2420–3010 of the HCV polyprotein (the NS5B protein) can be cloned into a vector, such as between the BamHI and HindIII sites of the pBlue BacIII vector (Invitrogen), and expressed in Sf9 cells by a baculovirus vector [International Patent Publication WO 96/37619; Behrens et al., EMBO J. 15:12–22 (1996)]. A baculovirus expression system has also been used to express a C-terminal histidine-tagged NS5B construct [Lohmann et al., J. Virol. 71:8416–28 (1997)].

In accordance with the present invention there may be employed conventional molecular biology, microbiology, and recombinant DNA techniques within the skill of the art for the production of NS5B. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis [M. J. Gait ed. (1984)]; Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; A Practical Guide To Molecular Cloning [B. Perbal (1984)]; Current Protocols in Molecular Biology, John Wiley & Sons, Inc. [F. M. Ausubel et al. (eds.) (1994)].

In addition to the preferred consensus NS5B described above, various mutant forms or homologues can be employed. The terms "mutant" and "mutation" mean any detectable change in genetic material, e.g. DNA, or any process, mechanism, or result of such a change. This includes gene mutations, in which the structure (e.g., DNA sequence) of a gene is altered, any gene or DNA arising from any mutation process, and any expression product (e.g., protein) expressed by a modified gene or DNA sequence. The term "variant" may also be used to indicate a modified or altered gene, DNA sequence, enzyme, cell, etc., i.e., any kind of mutant.

"Sequence-conservative variants" of NS5B are those in which a change of one or more nucleotides in a given codon position results in no alteration in the amino acid encoded at that position. "Function-conservative variants" of NS5B are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like).

Synthesis of RNA Oligonucleotide Template

As used herein, the term "oligonucleotide" refers to a nucleic acid, generally of at least 10, preferably at least 15, and more preferably at least 20 nucleotides, preferably no more than 100 nucleotides, that can serve as a template for NS5B, or which is produced as the result of NS5B polymerase activity. The oligonucleotide template of the invention is preferably RNA, since NS5B uses a DNA template poorly.

Generally, oligonucleotides for use as the template are prepared synthetically, preferably on a nucleic acid synthesizer. In a preferred embodiment, the oligonucleotide terminates in a nucleotide base that is modified to prevent further addition of bases, e.g., with a dideoxy nucleotide. This is to prevent primer-dependent polymerase activity by a copy-back mechanism, and to prevent coupling of labeled nucleotides to the 3' end of the template, resulting from template-independent TNTase activity. RNA template oligonucleotides can also be obtained from commercial sources (Oligos Etc., Inc., Wilsonville, Oreg.; Dharmacon Research, Inc., Boulder, Colo.; HHMI Biopolymer/Keck FBRL, Yale University, New Haven, Conn.; Baron Biotech, Milford, Conn.).

Oligonucleotides produced by NS5B activity can be labeled, e.g., with $^{32}$P-nucleotides or $^{33}$P-nucleotides. The presence of the label permits detection of nascent oligonucleotides, i.e., distinguishing them from the template. While $^{32}$P provides a stronger signal, $^{33}$P is easier to work with.

NS5B Activity Assays

Generally, NS5B polymerase activity assays must be run under conditions that permit polymerization. Generally, this requires the presence of a divalent cation, e.g., $Mg^{2+}$ or $Mn^{2+}$ as disclosed above, sufficient quantities of ribonucleotide triphosphates to serve as substrates for the polymerase, an RNA template as pointed out above, and the NS5B in an isotonically buffered aqueous solution. In a specific embodiment, the assay is performed in an optimal buffer containing 20 mM Tris.Cl, pH7.3, 0.65 mM $MgCl_2$, 5 mM $MnCl_2$, 5 mM DTT, 2% glycerol, 0.1% tween-20, 0.25% N-dodecyl-β-D-maltoside, 50 µg per ml of BSA, 0.25 µM of RNA template and 0.1 µM of HCV NS5B protein. An alternative buffer is 20 mM sodium glutamate, pH 8.2, 4 mM $MgCl_2$, 1 mM $MnCl_2$, 10 mM dithiothreitol (DTT), and 0.5% Triton X-100. The concentration of unlabeled NTPs is 200 µM, and the concentration of the labeled NTP is 0.15 µM. Any label can be used. Preferably the label is a phosphorous isotope, e.g., P-33 or P-32. P-32 will produce a stronger signal, but P-33 is easier to work with.

The reaction can be performed at room temperature (22° C.), although higher and lower temperatures are possible. For example, other polymerases are more efficient at 37° C. The reaction time can vary, depending on the rate of product formation, but should be long enough to permit at least one complete round of synthesis.

In a preferred embodiment, the reaction can be performed in the presence of candidate inhibitory compounds, e.g., to evaluate the ability of such compounds to inhibit NS5B activity. Such compounds, which may have been identified in a primary screen, e.g., by the ability to bind to NS5B or to inhibit NS5B activity (in a primer-dependent fashion), or which may be identified in a primary screen that takes advantage of de novo priming, are good lead candidates to develop anti-HCV pharmaceuticals.

As used herein, the term "compound" refers to any molecule or complex of more than one molecule that affects NS5B enzymatic function. The present invention contemplates screens for synthetic small molecule agents, chemical compounds, chemical complexes, and salts thereof as well as screens for natural products, such as plant extracts or materials obtained from fermentation broths.

In these assays, compounds with known replicase inhibitory activity can be used as positive controls. One example of such a compound is gliotoxin, which is a known poliovirus 3D RdRp inhibitor. Other such compounds include nucleotide analogs, such as dideoxy nucleotides, that inhibit synthesis. Preferably, however, an inhibitor or candidate inhibitor interferes specifically with the de novo initiation process.

High Throughput/Primary Screens

In one embodiment, a de novo assay system of the invention can be formatted in an automated high throughput screen (HTS) for primary screening of candidate anti-HCV NS5B compounds.

One example of a HTS screen of the invention is scintillation proximity assay (SPA). In such an assay, the RNA template may be biotinylated (e.g. at the 5' end) and the synthesized products are captured onto the streptavidin-coated SPA beads through their complementarity to the template RNA strand (i.e., forming RNA duplex). Incorporations of radiolabeled nucleotides are measured. Alternatively, biotinylated nucleotides can be used as substrates in the assay to provide a direct means of capturing the products using streptavidin-coated SPA beads.

Secondary/Mechanism Screens

While the discovery of de novo priming activity by NS5B provides for primary screening assays, particularly in an HTS format, a more important discovery of the invention is to use de novo, primer independent, HCV replicase activity as a probe for the mechanistic studies of candidate compounds discovered in a primary screen. In particular, the discovery that HCV NS5B initiates replication in a primer independent fashion provides incentive to identify NS5B inhibitory compounds that directly interfere with this process. An advantage of such candidate compounds is that they may be more effective than other types of replication inhibitors, because they target a unique rate-limiting step in HCV replication.

The replication assays described infra provide one means to further evaluate NS5B activity. These assays can be readily adapted for dose response or absolute (saturation) inhibition by possible anti-HCV NS5B compounds. For example, an assay system as described infra, comprising 20 mM Tris.Cl, pH7.3, 0.65 mM $MgCl_2$, 5 mM $MnCl_2$, 5 mM DTT, 2% glycerol, 0.1% tween-20, 0.25% N-dodecyl-β-D-maltoside, 50 µg per ml of BSA, 200 µM of ATP, CTP and GTP, 0.1 µM of α-$^{33}$P-UTP, 0.25 µM of RNA template and 0.1 µM of HCV NS5B protein can be set up in the presence and absence of a dilution series of candidate inhibitory compounds. The ability of such compounds to inhibit replication initiation or elongation can be detected, e.g., by running the reaction for about one hour, extracting the nascent, labeled RNA by phenol/chloroform extraction and ethanol precipitation, separating the nucleic acids on a 15–20% PAGE gel in 8M urea, and detecting products by autoradiography.

Alternatively, a memebrane binding assay in which the radiolabeled products are captured to a membrane may be used as the assay format.

EXAMPLES

The invention can be more fully understood by reference to the following examples, which are provided as exemplary of the invention and not limiting of the invention.

Example 1

De Novo Priming/Initiation Activity of HCV Replicase

Materials and Methods

Templates.

Synthetic RNA templates were prepared commercially (Oligos Etc., Inc., Wilsonville, Oreg.). The sequences of the templates were:

(+)21: 5'-UGGCCUCUCUGCAGAUCAUGU (di-H)-3' (SEQ ID NO:1)
c(+)21: 5'-UGGCCUCUCUGCAGAUCAUGUc (di-H)-3' (SEQ ID NO:2)
Temp III: 5'-CCUUUUCUAAUUCUCGUAUGCG(di-H)-3' (SEQ ID NO:3)

The (+)21 template corresponds to the 3' terminal sequence of HCV genomic (+)-strand RNA; c(+)21 contains an extra cytidylate at the 3' end. Temp III template corresponds to the 3' terminal sequence of BVDV (−)-strand RNA. All three RNA molecules contain a dideoxyribose in the 3' nucleotide. This modification renders them incapable of self-priming in RNA replication.

In Vitro Priming/Initiation Assay.

Each reaction contained 20 mM Tris.Cl, pH7.3, 0.65 mM $MgCl_2$, 5 mM $MnCl_2$, 5 mM DTT, 2% glycerol, 0.1% tween-20, 0.25% N-dodecyl-β-D-maltoside, 50 µg per ml of BSA, 200 µM of ATP, CTP and GTP, 0.1 µM of β-$^{33}$P-UTP or γ-$^{32}$P-GTP, 0.25 µM of RNA template and 0.1 µM of HCV NS5B protein (in a total volume of 40 µl). When γ-$^{32}$P-GTP was used as the labeling nucleotide, 50 µM of unlabeled GTP was included along with the radiolabeled GTP. The reactions were performed at room temperature for 1 hour, followed by phenol/chloroform extraction and ethanol precipitation. Labeled products were separated on a 15% PAGE/8 M urea gel and detected by autoradiography. High concentrations of nucleoside triphosphates, ATP and CTP for (+)21 and GTP and ATP for c(+)21, were required for de novo priming at +1 and +2 positions (numbered from the 3' end) for efficient synthesis.

Source of NS5B.

The NS5B used in these assays is a soluble, His-tagged form of the protein expressed in *E. coli*, as described in Ferrari et al. [J. Virol. 73:1649–1654 (1999)], which is specifically incorporated herein by referenced in its entirety.

Results

To demonstrate this de novo priming activity, three RNA templates [(+)21, c(+)21 and Temp III] containing either HCV or BVDV 3' terminal sequence were chemically synthesized. The 3' end nucleotides of the RNAs were substituted with the corresponding dideoxy-nucleotides (2', 3') in order to eliminate any self-priming via a "copy-back" mechanism. Results in FIG. 1 showed that HCV NS5B RdRp was able to utilize these modified RNA templates to initiate RNA replication, producing RNA products of different sizes. The monomer-size products (21 or 22 base long respectively, denoted by "*") represent the full-length RNA copies of the input templates, which can only result from primer-independent de novo initiation. Such an initiation of RNA replication directly from nucleotides represents a novel priming activity. Some smaller and larger products were also generated during the de novo RNA replication, representing, probably, products of abortive initiation and products of stuttering elongation of nascent RNA by the RdRp.

Figure 2:
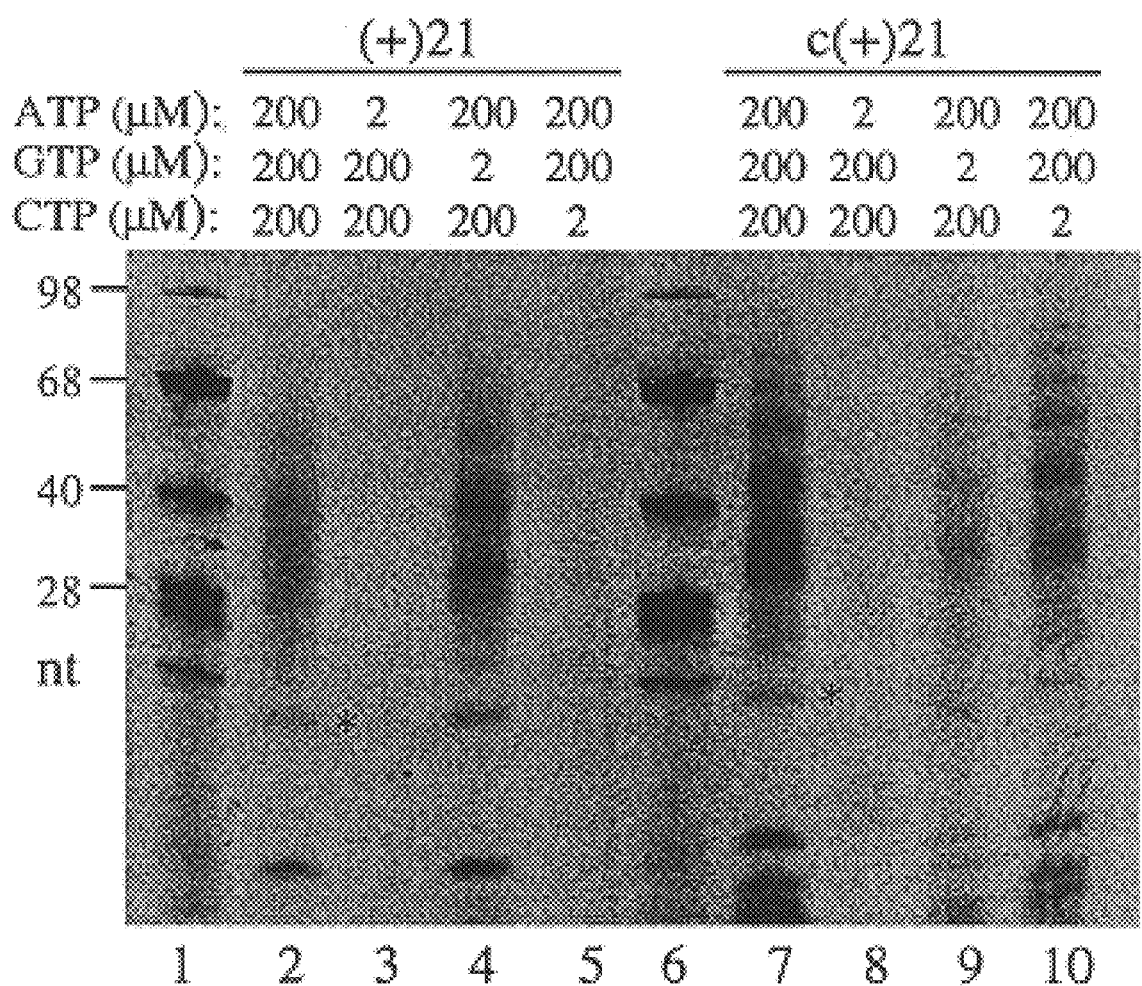
FIG. 2 shows that high concentrations of initiation nucleotides (at positions +1 and +2) are required for de novo synthesis. Lanes 1 and 6 are molecular weight markers. Lanes 2–5 used the (+)21 template (SEQ ID NO:1), which terminates with a -GU-3' sequence. Lanes 7–10 used the C(+)21 template, which terminates with a -UC-3' sequence. Lanes 2 and 7 are positive controls (ATP, GTP and CTP are present at 200 $\mu$M). In lanes 3 and 8, ATP is limiting (2 $\mu$M). In lanes 4 and 9, GTP is limiting (2 $\mu$M). In lanes 5 and 10, CTP is limiting (2 $\mu$M). * indicates a template sized product.

We further demonstrated that this de novo RNA replication by HCV NS5B required high concentrations of nucleoside triphosphates corresponding to +1 and +2 positions from the 3' ends (FIG. 2): (+)21 RNA ( - - - GU 3') required high concentrations of ATP and CTP while c(+)21 RNA ( - - - UC 3') required high concentrations of GTP and ATP for efficient RNA synthesis. This suggests that efficient de novo priming at the 3' end of the RNA templates is concentration sensitive and the priming step may be a rate-limiting one during RNA replication.

Figure 3:
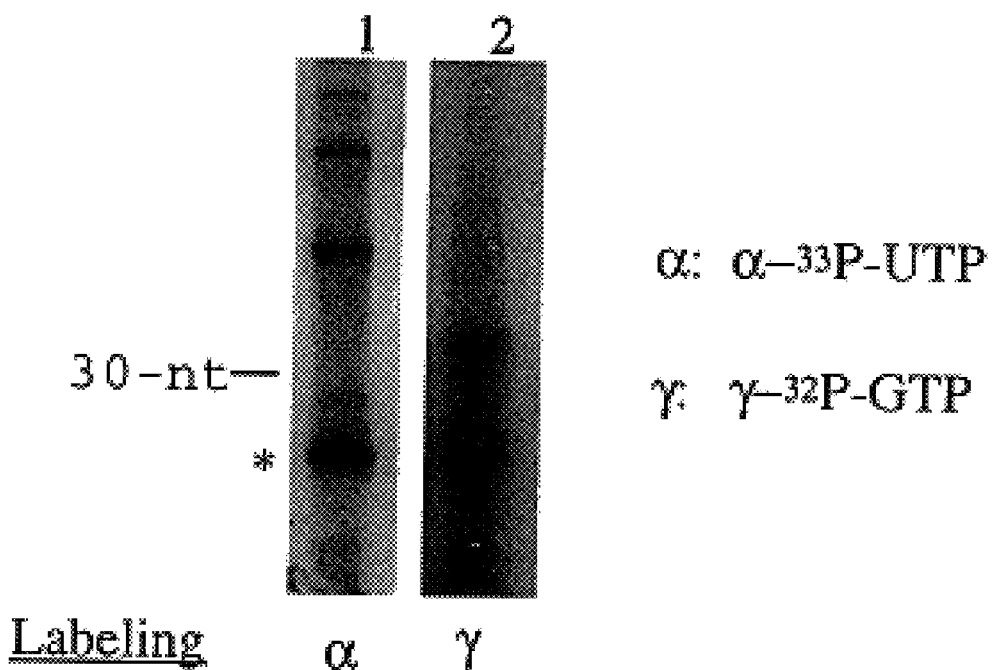
FIG. 3 shows that de novo replication products can be labeled by $\gamma$-$^{32}$P-GTP. A similar labeling pattern was observed with $\gamma$-$^{32}$P-GTP (lane 2) as the labeling nucleotide compared to the $\alpha$-$^{33}$P-UTP (lane 1) labeling. Labeling will the $\gamma$-P will result in labeling of only the initial NTP, since the $\gamma$-P is lost with pyrophosphate during polymerization by the replicase (i.e., only the de novo synthesized products will be labeled).

We further confirmed that the reaction products are indeed derived from de novo replication by labeling with γ-$^{32}$P-GTP (FIG. 3). Labeling with the γ-$^{32}$P will result in labeling of only the initial NTP, since the γP is lost with pyrophosphate during polymerization by the replicase.

The present invention is not to be limited in scope by the specific examples disclosed herein. Various embodiments and alternatives are part of this invention, the full scope of which is delineated by the claims appended hereto.

All sizes and molecular weights are provided for the sake of convenience in understanding the invention, and should be regarded as approximate and not limiting thereof.

Patents, patent applications, references, and methods cited in this application are incorporated herein by reference in their entireties.

What is claimed is:

1. An assay system for hepatitis C virus (HCV) primer independent replicase activity, which assay system comprises an RNA template which is modified to prevent copy-back priming, an enzymatically active amount of HCV non-structural protein 5B (NS5B), ATP, GTP, CTP, and UTP nucleotide triphosphate (NTP) bases, wherein one of the NTP bases is radiolabeled, and an assay buffer that supports replication activity of NS5B.

2. The assay system of claim 1, wherein the NS5B is a soluble NS5B expressed in *Escherichia coli*.

3. The assay system of claim 1, wherein the RNA template contains a dideoxy nucleotide at the 3' terminus.

4. The assay system of claim 1, wherein the label is a radioactive phosphate.

5. The assay system of claim 1, wherein the labeled base is α-$^{33}$P-NTP that hydrogen bonds to a base in the template.

6. The assay system of claim 1, wherein the labeled base is a γ-$^{32}$P-NTP that hydrogen bonds to a terminal or a penultimate 3' base.

7. The assay system of claim 1, wherein the assay buffer comprises 20 mM Tris.Cl, pH7.3, 0.65 mM $MgCl_2$, 5 mM $MnCl_2$, 5 mM DTT, 2% glycerol, 0.1% tween-20, 0.25% N-dodecyl-β-D-maltoside, 50 µg per ml of BSA, 200 µM of NTPs, and the assay is performed at 22° C.

8. The assay system of claim 1, wherein the RNA template has a sequence selected from the group consisting of
UGGCCUCUCUGCAGAUCAUGU (SEQ ID NO:1),
UGGCCUCUCUGCAGAUCAUGUC (SEQ ID NO:2), and
CCUUUUCUAAUUCUCGUAUGCG (SEQ ID NO:3).

9. A method for detecting primer independent hepatitis C virus (HCV) replicase activity, which method comprises detecting the presence of a nucleic acid synthesized by an HCV non-structural protein 5B (NS5B) on an RNA template that is incapable of forming a copy-back structure in the presence of ATP, GTP, CTP, and UTP nucleotide triphosphate (NTP) bases, wherein one of the NTP bases is radiolabeled, and an assay buffer that supports replication activity of NS5B.

10. The method according to claim 9, wherein detecting the nucleic acid synthesized by NS5B comprises evaluating an autoradiograph of reaction products separated by gel electrophoresis.

11. The method according to claim 9, wherein the NS5B is a soluble NS5B expressed in *Escherichia coli*.

12. The method according to claim 9, wherein the RNA template contains a dideoxy nucleotide at the 3' terminus.

13. The method according to claim 9, wherein the label is a radioactive phosphate.

14. The method according to claim 9, wherein the labeled base is a α-$^{33}$P-NTP that hydrogen bonds to a base in the template.

15. The method according to claim 9, wherein the labeled base is a γ-$^{32}$P-NTP that hydrogen bonds to a terminal or a penultimate 3' base.

16. The method according to claim 9, wherein the assay buffer comprises 20 mM Tris.Cl, pH7.3, 0.65 mM MgCl$_2$, 5 mM MnCl$_2$, 5 mM DTT, 2% glycerol, 0.1% tween-20, 0.25% N-dodecyl-β-D-maltoside, 50 μg per ml of BSA, 200 μM of NTPs, and the assay is performed at 22° C.

17. The method according to claim 9, wherein the RNA template has a sequence selected from the group consisting of
UGGCCUCUCUGCAGAUCAUGU (SEQ ID NO:1),
UGGCCUCUCUGCAGAUCAUGUC (SEQ ID NO:2), and
CCUUUUCUAAUUCUCGUAUGCG (SEQ ID NO:3).

18. The method according to claim 9, further comprising limiting the amount of one nucleotide triphosphate that hydrogen bonds to a base at least three bases from the 3' end of the RNA template.

19. A composition comprising an HCV NS5B protein and an RNA template which is incapable of forming a copy-back structure.

20. The composition of claim 19 which is in an assay buffer that supports replication activity of NS5B.

* * * * *